(12) United States Patent  
Jimenez et al.

(10) Patent No.: US 7,917,986 B2
(45) Date of Patent: Apr. 5, 2011

(54) TOOTHBRUSH

(75) Inventors: Eduardo J. Jimenez, Manalapan, NJ (US); John Jacob Gatzemeyer, Hillsborough, NJ (US); Christine Enderby, Portland, OR (US); Trent Kahute, Charlestown, MA (US)

(73) Assignee: Colgate-Palmolive Company, New York, NY (US)

( * ) Notice: Subject to any disclaimer, the term of this patent is extended or adjusted under 35 U.S.C. 154(b) by 1279 days.

(21) Appl. No.: 11/460,184

(22) Filed: Jul. 26, 2006

(65) Prior Publication Data

US 2007/0050931 A1 Mar. 8, 2007

Related U.S. Application Data (60) Provisional application No. 60/702,381, filed on Jul. 26, 2005.

(51) Int. Cl.
*A46B 9/04* (2006.01)
(52) U.S. Cl. .............................. 15/167.1; 15/22.1; 15/246
(58) Field of Classification Search ............... 15/143.1, 15/167.1, 184, 257.01, 246, 247, 22.1, 28; 132/308, 311; D4/104, 107, 108, 125, 126; D6/528, 534
See application file for complete search history.

(56) References Cited

U.S. PATENT DOCUMENTS

| 632,445 | A | 9/1899 | Craig, Jr. |
| 634,906 | A | 10/1899 | McCloskey |
| 657,858 | A | 9/1900 | Cornelius |
| 1,178,147 | A | 4/1916 | Gardner |
| 1,690,311 | A | * | 11/1928 | Reich .................... 206/362.3 |
| D190,850 | S | | 7/1961 | Strachan |
| 3,325,847 | A | * | 6/1967 | Meranto ..................... 15/184 |
| 4,283,808 | A | | 8/1981 | Beebe |
| D279,941 | S | | 8/1985 | Anglin, Jr. |
| 4,602,650 | A | | 7/1986 | Pipkin |
| 4,872,721 | A | | 10/1989 | Sniadach |
| D308,740 | S | | 6/1990 | Leiter |
| D330,979 | S | | 11/1992 | Gruberg |
| D351,286 | S | | 10/1994 | Tapocik |
| D351,732 | S | | 10/1994 | Dair et al. |
| 5,444,889 | A | * | 8/1995 | Barre ........................ 15/167.1 |
| D379,280 | S | | 5/1997 | Butler et al. |
| 5,669,097 | A | | 9/1997 | Klinkhammer |
| 5,771,521 | A | * | 6/1998 | McNamee .................. 15/184 |
| 5,779,046 | A | | 7/1998 | Plakos |
| 5,876,134 | A | | 3/1999 | Tseng et al. |
| D410,787 | S | | 6/1999 | Barre et al. |
| D411,770 | S | | 7/1999 | Jesiolowski |
| 5,924,567 | A | | 7/1999 | Wenum |
| 5,926,901 | A | | 7/1999 | Tseng et al. |
| D413,444 | S | | 9/1999 | Weiss |

(Continued)

FOREIGN PATENT DOCUMENTS

DE 28 40 429 3/1980

(Continued)

*Primary Examiner* — Dung Van Nguyen
(74) *Attorney, Agent, or Firm* — Judy W. Chung (57) ABSTRACT

An oral care implement, such as an electric toothbrush, is ergonomically configured for the anatomical structures of children. In one embodiment, a toothbrush is provided with three dimensional sections in visually appealing or recognizable shapes for promoting more frequent of brushing by children. In another embodiment, a toothbrush includes user replaceable sections or covers that allow a user to selectively tailor the visual appearance of their own toothbrush or allow for increased exposure of other products by providing surface areas for placement of advertising or other promotional material.

21 Claims, 9 Drawing Sheets

U.S. PATENT DOCUMENTS

| | | | |
|---|---|---|---|
| D418,302 S | | 1/2000 | Landauer |
| 6,015,328 A | * | 1/2000 | Glaser ........................ 446/72 |
| 6,026,532 A | | 2/2000 | Catanzaro |
| 6,102,203 A | | 8/2000 | Marro |
| 6,129,090 A | | 10/2000 | Pillar et al. |
| D433,570 S | | 11/2000 | Landauer |
| 6,202,242 B1 | | 3/2001 | Salmon et al. |
| 6,318,685 B1 | | 11/2001 | Huber |
| 6,325,626 B1 | | 12/2001 | Blass |
| 6,360,395 B2 | | 3/2002 | Blaustein et al. |
| D456,141 S | | 4/2002 | Landauer |
| 6,371,294 B1 | | 4/2002 | Blaustein et al. |
| 6,393,626 B1 | | 5/2002 | Dhillon |
| D458,759 S | | 6/2002 | Landauer |
| 6,422,867 B2 | | 7/2002 | Lang et al. |
| 6,446,294 B1 | | 9/2002 | Specht |
| 6,457,583 B1 | | 10/2002 | Tee et al. |
| 6,461,164 B1 | | 10/2002 | Ramelli |
| D467,433 S | | 12/2002 | Massari et al. |
| 6,564,940 B2 | | 5/2003 | Blaustein et al. |
| 6,588,042 B2 | | 7/2003 | Fritsch et al. |
| D477,948 S | | 8/2003 | Paik |
| 6,601,272 B2 | | 8/2003 | Stvartak et al. |
| 6,687,940 B1 | | 2/2004 | Gross et al. |
| 6,709,185 B2 | | 3/2004 | Lefevre |
| D489,185 S | | 5/2004 | Kemp et al. |
| 6,779,216 B2 | * | 8/2004 | Davies et al. ................ 15/22.1 |
| 2003/0000030 A1 | | 1/2003 | Davies et al. |
| 2003/0019063 A1 | | 1/2003 | Abraham |
| 2003/0028987 A1 | | 2/2003 | Morawski et al. |
| 2003/0166373 A1 | | 9/2003 | Whitney et al. |
| 2003/0213075 A1 | | 11/2003 | Hui et al. |
| 2005/0109364 A1 | | 5/2005 | Gross et al. |

FOREIGN PATENT DOCUMENTS

| | | |
|---|---|---|
| GB | 2 167 995 | 6/1986 |
| JP | 51-38561 | 9/1974 |
| WO | WO 01/52695 | 7/2001 |
| WO | WO 2004/037107 | 5/2004 |
| WO | WO 2004/039205 | 5/2004 |

* cited by examiner

TOOTHBRUSH

CROSS REFERENCE TO RELATED APPLICATIONS

This is application claims the benefit of priority of U.S. patent application No. 60/702,381, filed Jul. 26, 2005, the contents of which are expressly incorporated by reference herein.

FIELD OF THE INVENTION

The present invention pertains to an oral care implement, and more particularly, to a powered toothbrush configured for ease of use.

BACKGROUND OF THE INVENTION

Powered toothbrushes generally have a movable head that is motor-driven from a handle. While such toothbrushes usually achieve a more intensive cleaning action than manual toothbrushes, they may be uncomfortable for users due to transmission of motor vibrations to the hand of the user.

These problems are magnified in that adult powered toothbrushes may be uncomfortable for some users, such as children. In particular, the anatomical structure of children generally provides insufficient musculoskeletal strength or control of the hands or fingers to effectively manipulate adult electric toothbrushes. Further, the differences in the oral cavity size and tooth configurations between children and adults make it difficult for children to use adult toothbrushes. Hence, there is a need for an oral care implement ergonomically configured for children.

BRIEF SUMMARY OF THE INVENTION

There is provided an ergonomic toothbrush for the anatomical structures of children.

In one embodiment, a resilient sleeve covers at least a portion of a toothbrush handle to provide comfort for the user. In other embodiments, a resilient sleeve has three-dimensional sculpture shapes or two dimensional graphics to provide a visually appealing product with reduced vibration transmission to a user's hand.

In another embodiment, a toothbrush includes user replaceable sections or covers enabling selective tailoring of the visual appearance. In yet another embodiment, a toothbrush is configured for exposure of products by providing regions for placement of advertising or other promotional material. In one embodiment, a toothbrush has three dimensional sections in visually appealing or recognizable shapes for promoting more frequent brushing by children. Other embodiments include other features as a way of enticing children to become interested in the toothbrush and brushing in general.

DETAILED DESCRIPTION

Figure 1:
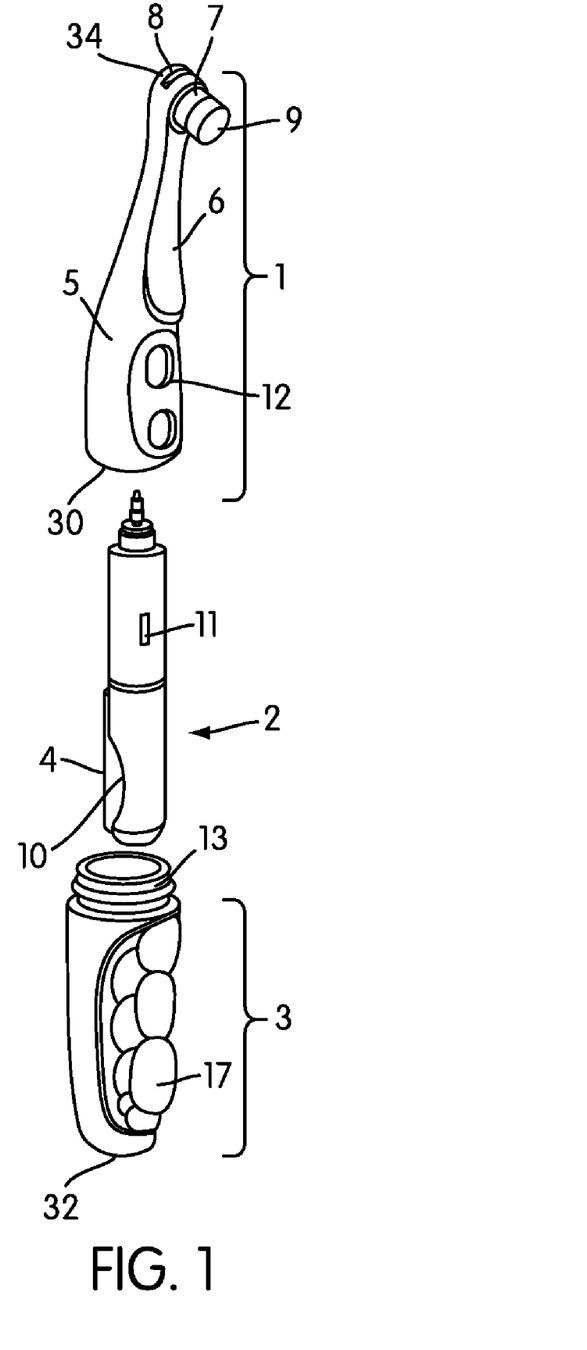
FIG. 1 is an exploded assembly view of a toothbrush in accordance with one embodiment of the present invention.

Referring to FIG. 1, a powered toothbrush includes a handle or grip body collectively defined by a top portion 1 and a base portion 3. The handle can be defined by a unitary molded construction or two handle halves or other multiple components. An internal motor chassis 2 and a power source such as a battery 4 are retained within a cavity in the handle formed by the top and base portions 1, 3.

Figure 2:
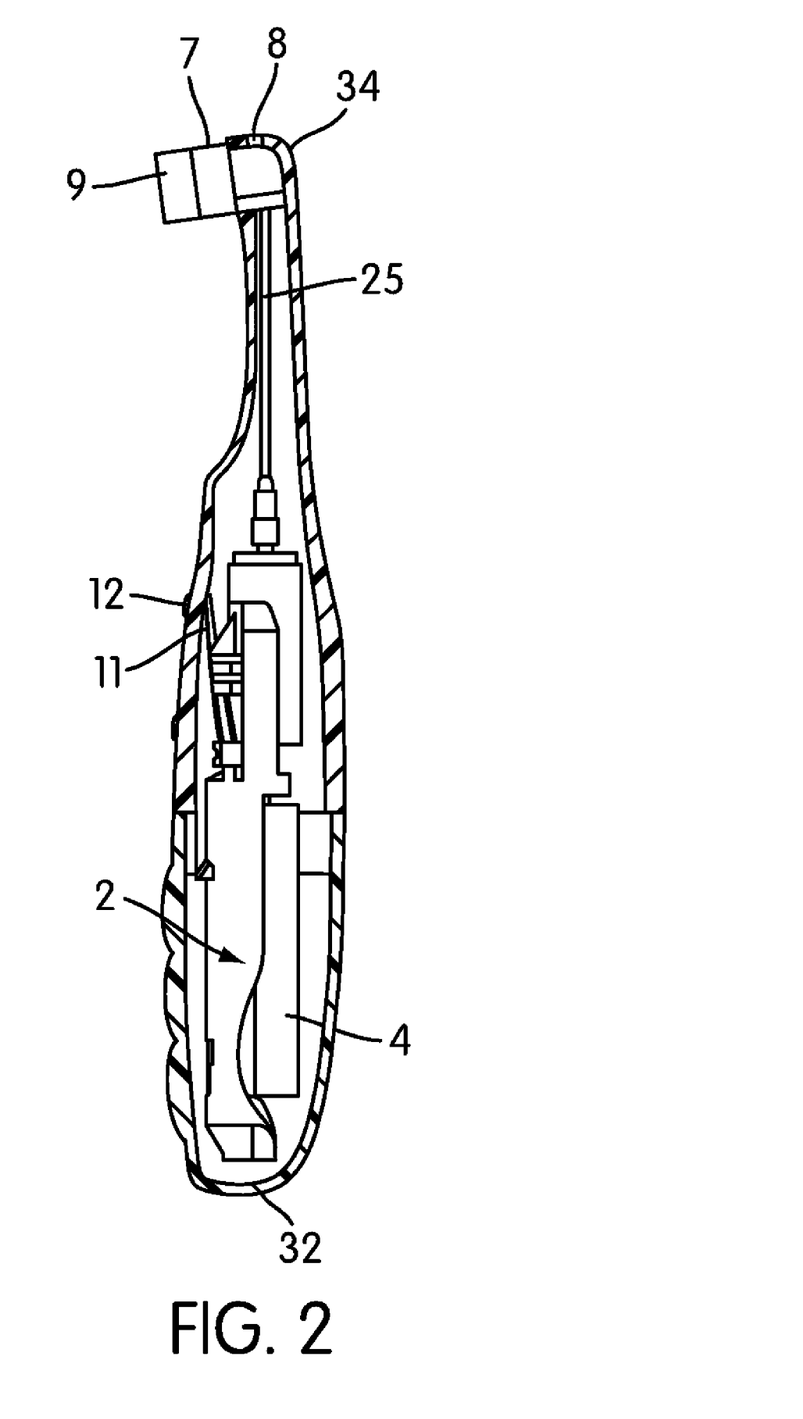
FIG. 2 is a cross section view from the side of an assembled toothbrush of FIG. 1.

Top portion 1 includes a handle upper portion 5 connected to a neck portion 6 and a rotating head 7 provided with tooth cleaning elements 9. Referring to FIGS. 1 and 2, the neck portion 6 generally extends from where the handle upper portion 5 begins to taper inwardly toward the shaft 25 (FIG. 2), to the base of the head 7. Head 7 is operatively connected to the internal motor chassis 2 by any desired construction such as, for example, by a shaft 25, and can provide tooth cleaning movement, such as vibrations, oscillations and the like. Non-limiting examples of tooth cleaning elements 9 can include filament bristles or elastomeric fingers or walls which are used for wiping, cleaning and/or massaging the user's oral tissue.

Base portion 3 includes a mating portion 13 that reliably mates with a complementary mating portion 30 of the top portion 1 so as to enclose the internal motor chassis 2 and other components. Mating portion 13 includes an "O" ring seal for providing water tightness in the handle cavity and/or for a snug interference fit between the top portion 1 and base portion 3. Other mating connections are possible.

As shown in FIG. 2, an outer switch section 12 is provided for activating and deactivating the motor 2 and movement of tooth cleaning elements 9. Outer switch 12, such as a push button, contacts and causes an interior switch 11 to activate the internal motor of internal motor chassis 2. Outer switch 12 comprises an outer layer polymeric material that is preferably shaped in an ornamental nature (e.g., stars, swirls, flowers) with other ornamental features along a specific theme as will be discussed below.

In one embodiment, a ratio of the length of the neck portion 6 and head 7 to the height of the toothbrush (measured from the distal bottom end 32 of base portion 3 to the distal top 34 of head section 7) ranges from 1:10 to 2:5. In another non-limiting example, the noted neck/head length to the toothbrush height ratio ranges from 1:20 to 1:30, with other ratios being possible. In one embodiment, the external height of the toothbrush ergonomically sized for a child ranges from about 160 cm to 200 cm. In other non-limiting embodiments, the height of a toothbrush ranges from about 160 cm to 194 cm; to less than 194 cm, with other heights being possible. In one embodiment, the width of the handle can range between 19 cm to 28 cm. In another embodiment, the depth of the handle ranges between 19 cm to 27 cm, or between 19 cm to 21 cm. These ergonomic configurations provide for a toothbrush to have a neck/head to length ratio to reach within the depth of the oral cavity, while balancing the need for musculoskeletal strength of a child to manipulate the toothbrush. Accordingly, these configurations or combination thereof enable a lightweight and easily maneuverable electric toothbrush for children.

Figure 3:
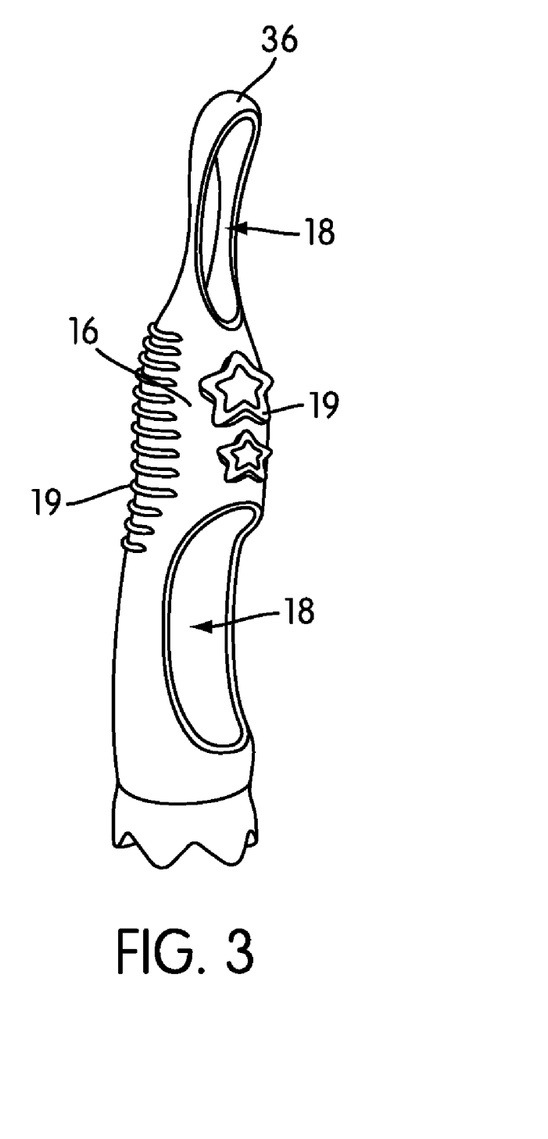
FIG. 3 is a perspective view of a sleeve construction in accordance with one embodiment of the present invention.
Figure 4:
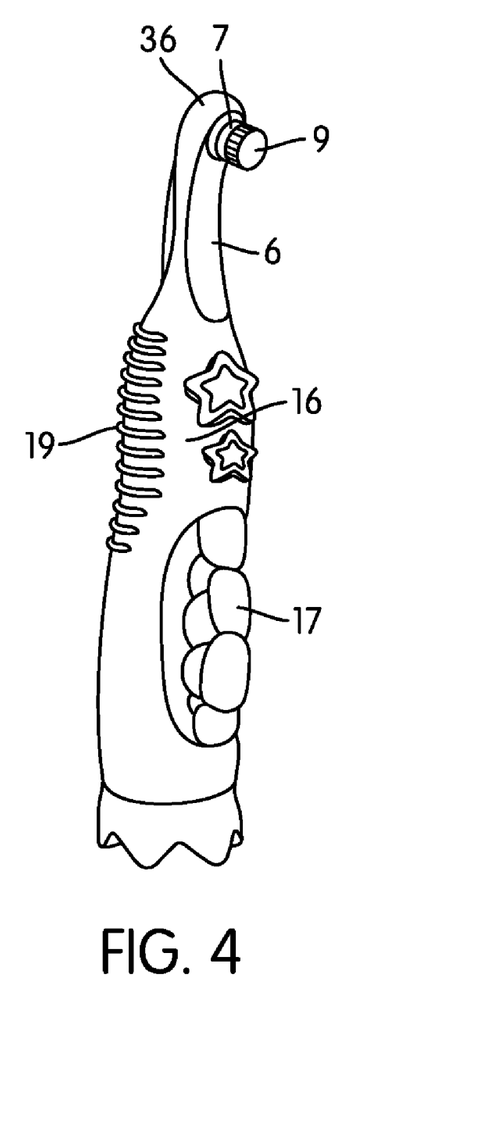
FIG. 4 is a schematic representation of a toothbrush with an attached sleeve of FIG. 3.

As shown in FIGS. 3-4, a resilient sleeve 16 is configured to fit over an electric toothbrush. Sleeve 16 provides for increased user comfort by dampening vibration transmissions of the electric toothbrush to the hand of the user, and/or provides obvious ornamental appearance benefits that are found particularly attractive by children. Of course, sleeve 16 can be used with manual toothbrushes as desired to impart aesthetic appeal. A distal end 36 of sleeve 16 extends along a portion of the head 7, and in one embodiment attaches to a connection portion 8 at the distal top 34 of the head 7 (FIG. 1) for an interference or snug fit. In such a construction, the sleeve 16 has a tab or protrusion (not shown) which extends away from the inside surface of the sleeve so as to be received in the connection portion 8 of the toothbrush. The connection portion 8 can be an appropriately sized depression or notch in the toothbrush head 7. Of course, the sleeve 16 may attach to head 7 in other ways as desired.

The sleeve 16 is preferably constructed from a resilient material including, but not limited to a thermoplastic elastomer, rubber, SANTOPRENE® and the like. Other resilient materials may be used based on specific desired sleeve properties, including but not limited to a desired Shore Hardness A rating, such as between 20-30. In one embodiment, the sleeve 16 is formed with three dimensional contouring 19 along a predetermined theme. For example, the theme may be simulations of characters, celebrities, cartoon or other animated characters, mass media figures, geometric figures, logos, or other such shapes. The sleeve 16 has an outer topography with sufficient physical shape variations in the contour, holes or apertures to create a sculptured three-dimensional appearance. In another embodiment, the sleeve 16 may be designed to provide a large surface area on which can be placed advertising or other promotional material. For example, the exposed outer surface or portions of the outer surface of the sleeve 16 are enabled to receive graphical labeling. In one embodiment, the outer surface or portions of sleeve 16 can be generally smooth for receiving the labeling.

As shown in FIGS. 3 and 4, in one embodiment, sleeve 16 may contain one or more opened areas or apertures 18 through the thickness which is devoid of sleeve material. One of the aperture features 18 of sleeve 16 exposes the external portion of graphical section 17 of the toothbrush (e.g., three-dimensional or two-dimensional graphical features), and is provided to be complementary to one or more graphical sections 17 on the bottom portion 3 of the toothbrush handle. As seen in the FIG. 3, the aperture 18 for the bottom portion is devoid of the material in the front of the toothbrush, but is preferably closed in the rear side of the toothbrush. The closed rear side enables, for example, improved gripping of the toothbrush. Nevertheless, the opened area 18 can be provided for other portions such as the top portion of the toothbrush handle as shown.

Figure 5A:
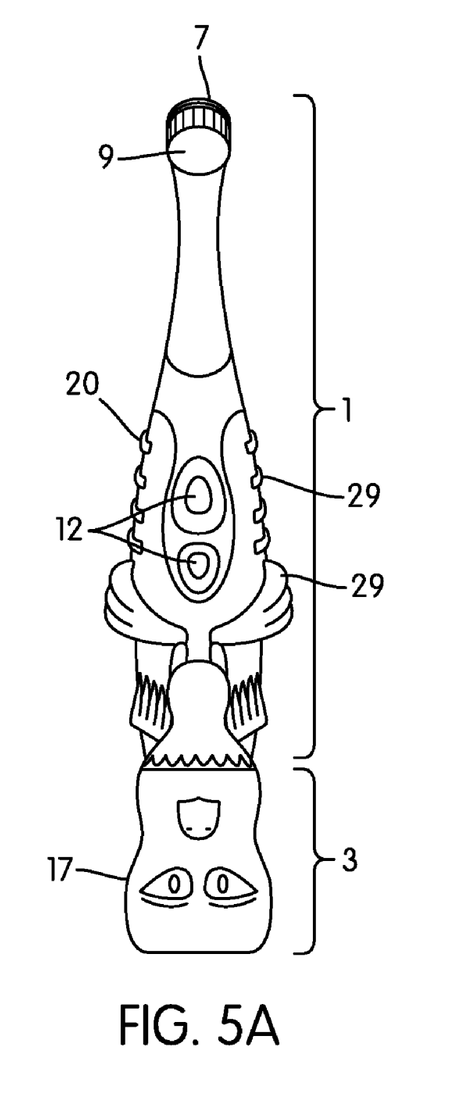
FIGS. 5A and 5B are illustrative front and side views of toothbrushes in accordance with one embodiment of the present invention.
Figure 5B:
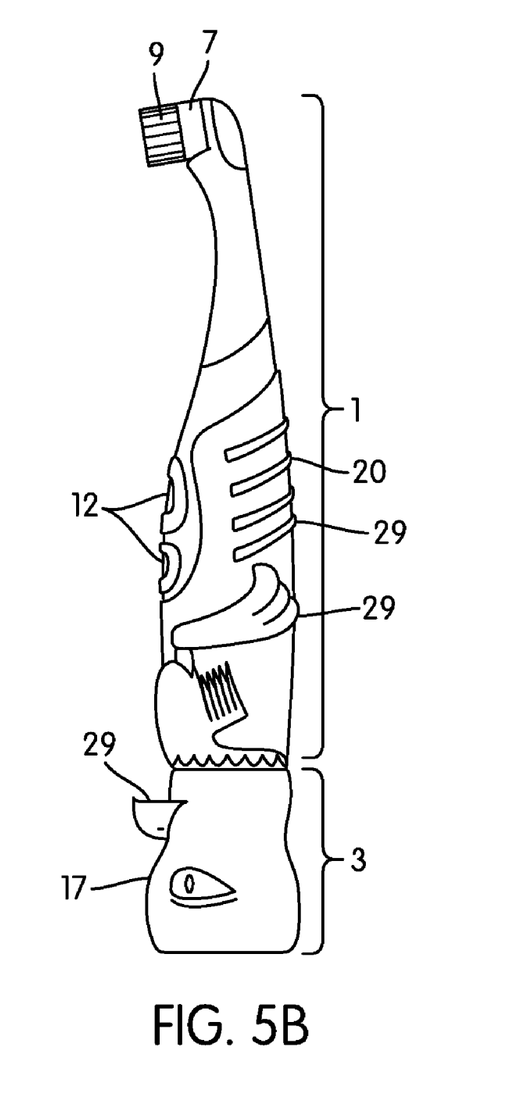
Figure 6A:
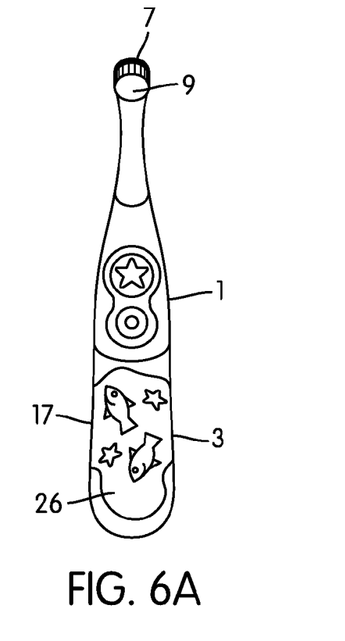
FIGS. 6A and 6B are illustrative front and side views of toothbrushes in accordance with one embodiment of the present invention.
Figure 6B:
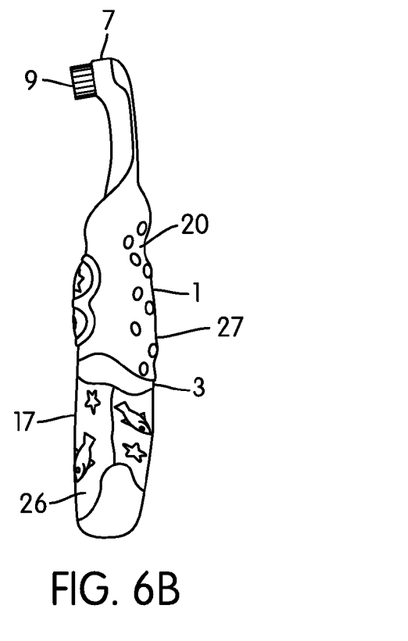
Figure 7A:
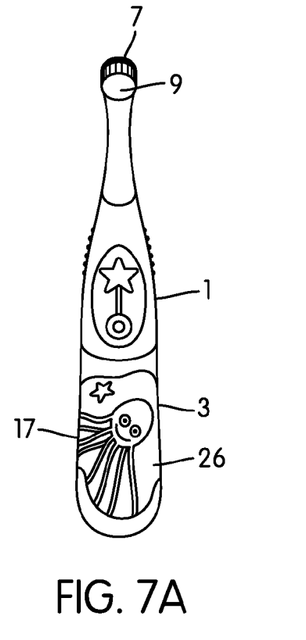
FIGS. 7A and 7B are illustrative front and side views of toothbrushes in accordance with one embodiment of the present invention.
Figure 7B:
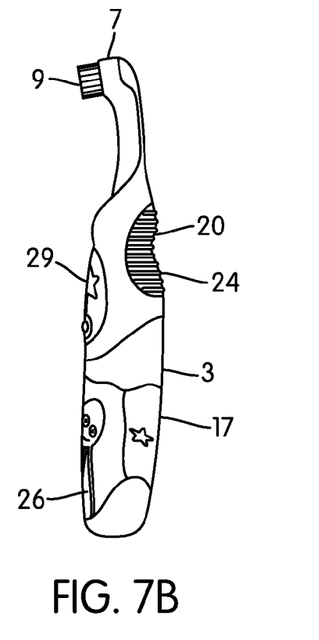
Figure 8A:
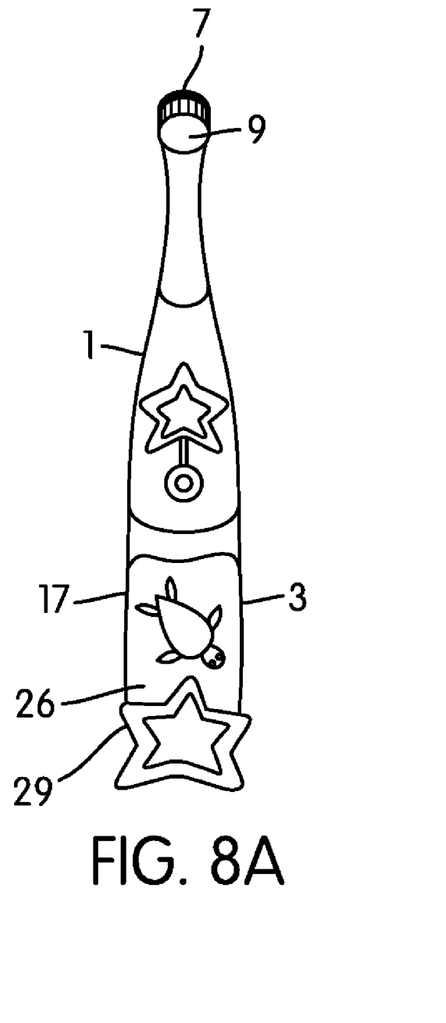
FIGS. 8A and 8B are illustrative front and side views of toothbrushes in accordance with one embodiment of the present invention.
Figure 8B:
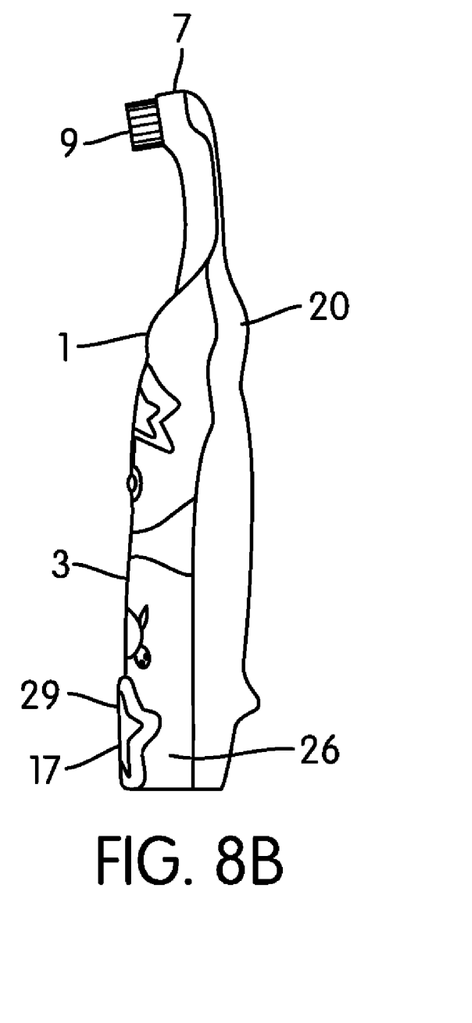

In one embodiment, the graphical section 17 is composed of a material and construction to provide an ornamental aesthetic shape. The graphical section 17 can be molded with the base portion 3 thereby forming a generally unitary element (FIGS. 5A-5B). In another embodiment, the graphical section 17 can be formed with an elastomeric material having a Shore hardness A value ranging from 20 to 30. In alternative embodiments shown in FIGS. 6A-8B, graphical section 17 is a replaceable and/or interchangeable insert for the base portion 3. In such an interchangeable construction, the graphical section may be formed as a resilient contoured removable plate 26.

In one embodiment, the bottom portion 3 can be of a contoured shape in order to provide a thematic representation with the remainder of the toothbrush handle, such as the top portion 1. The bottom portion 3 can be composed of a polymeric or elastomeric material 29 that provides a three dimensional visual representation, alone or in combination with a three dimensional shape of top portion 1. In such a construction, bottom portion 3 can have a three dimensional shape and/or color which resemble cartoon characters, logos, mass media figures, sports team mascots and the like along the overall entertainment theme of the toothbrush. For example, in FIGS. 5A and 5B, the toothbrush generally simulates a stylized representation of a totem pole or a cartoon bird. In particular, the bottom portion 3 of the toothbrush resembles a head of a cartoon bird and the remainder of the toothbrush handle resembles the body of a cartoon bird. In this way, a child is more apt to regularly use toothbrushes that are not only more comfortable, but are also visually appealing with shapes or colors.

In another embodiment, the top portion 1 of a toothbrush includes a finger rest region 20 provided in a depression (FIGS. 5B, 6B, 7B, and 8B). This enables a user to reliably control the direction of toothbrush in the oral cavity and provide better pressure application to the oral tissue. In an embodiment, the rest region 20 has a tactile feature to increase the friction on the user's finger surfaces and enhance the user's ability to grip the handle, particularly under wet conditions. In other embodiments, the rest region 20 includes projections 22 (FIG. 7B) or strip projections 24 (FIG. 8B), to provide improved user control while minimizing accidental slipping through a user's finger.

Figure 9A:
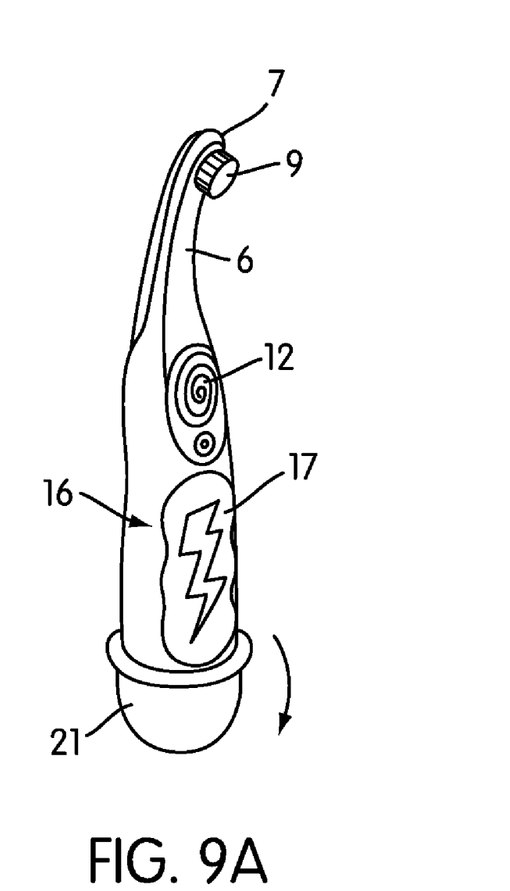
FIGS. 9A and 9B are a schematic representation of a sleeve construction in accordance with one embodiment of the present invention.
Figure 9B:
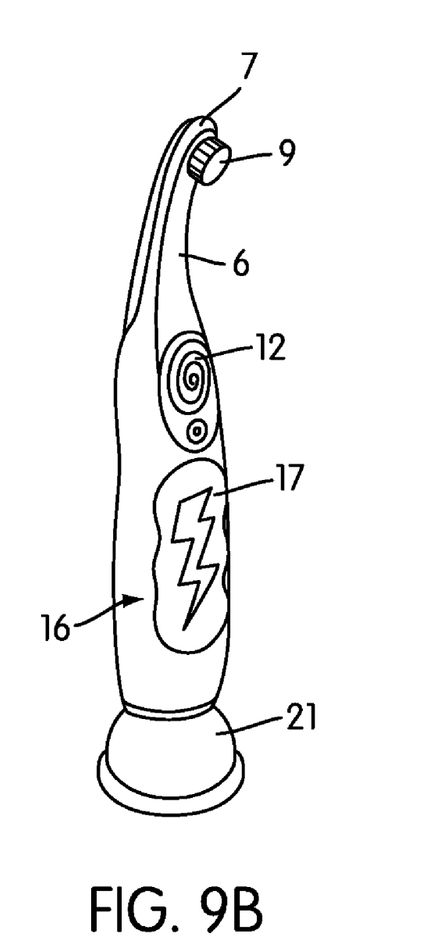
Figure 10:
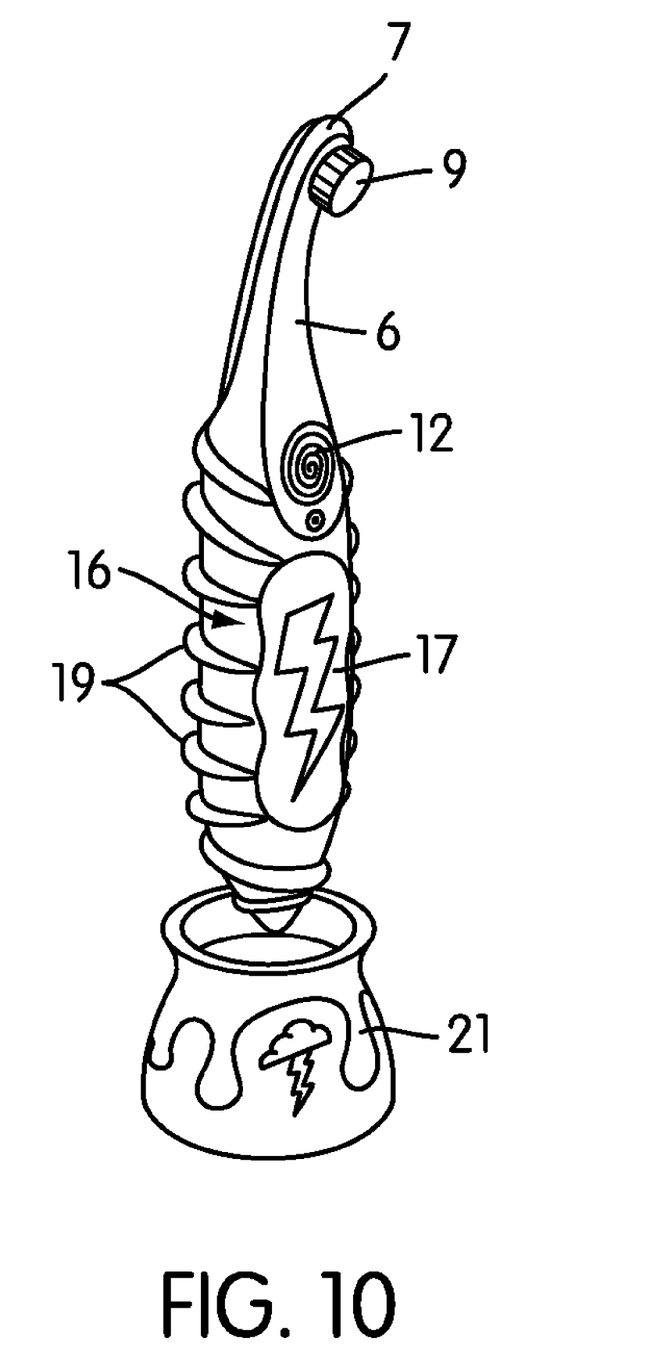
FIG. 10 is a schematic representation of a toothbrush with a sleeve construction in according with one embodiment of the present invention.

In one embodiment shown in FIGS. 9A, 9B and 10, sleeve 16 includes a stand 21, on which the toothbrush can be placed when not in use to avoid contacting head section 7 or bristles 9 with germs, bacteria, or other infectious agents present on restroom surfaces. Stand 21 may be integrally molded with sleeve 16 to a resilient releasable construction. In operation, the releasable stand 21 flips from a rest or first position along sleeve 16 (FIG. 9A) to a deployed position (FIG. 9B). Hence, the stand 21 is able to flip open into an in-use deployed position to hold the toothbrush substantially upright. In FIG. 10, stand 21 could be a separate component with three-dimensional contouring and can be connected to the remainder of sleeve 16 using any appropriate connecting methods known to those in the art.

Figure 11:
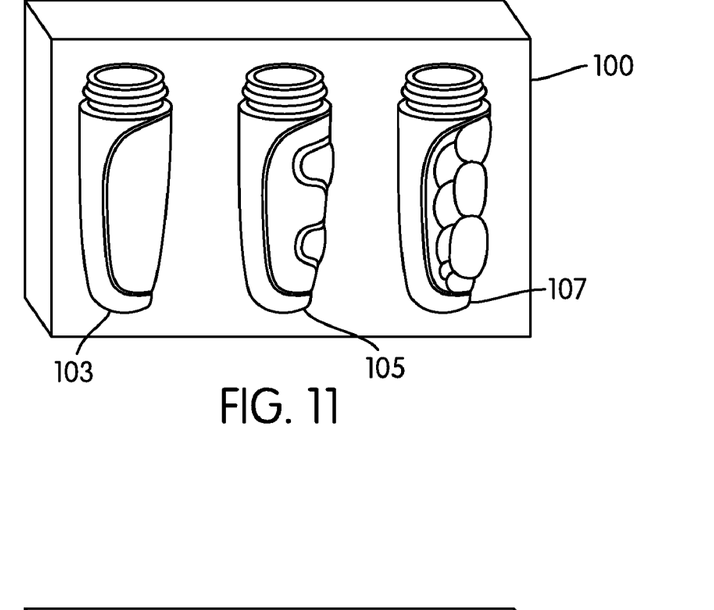
FIGS. 11 and 12 are schematic representations of oral care systems in accordance with various embodiments of the present invention.

In one embodiment illustrated in FIG. 11, a plurality of base portions 103-107 or graphical sections, can be sold or otherwise provided together as a system or kit 100 along a predetermined theme. Accordingly, the toothbrush and base portions 103-107 or graphical sections can be provided in an enclosure, such as box. In other constructions, a plurality of sleeves and/or base portions, alone or in combination may be provided in specific packages or subject area classifications, such as professional and amateur sports, entertainment, music, motion picture, business, print and electronic media, politics, or computing gaming, for example. In this way, toothbrush advantageously enhances a child's ability to use their imagination in a positive manner to improve oral care.

Figure 12:
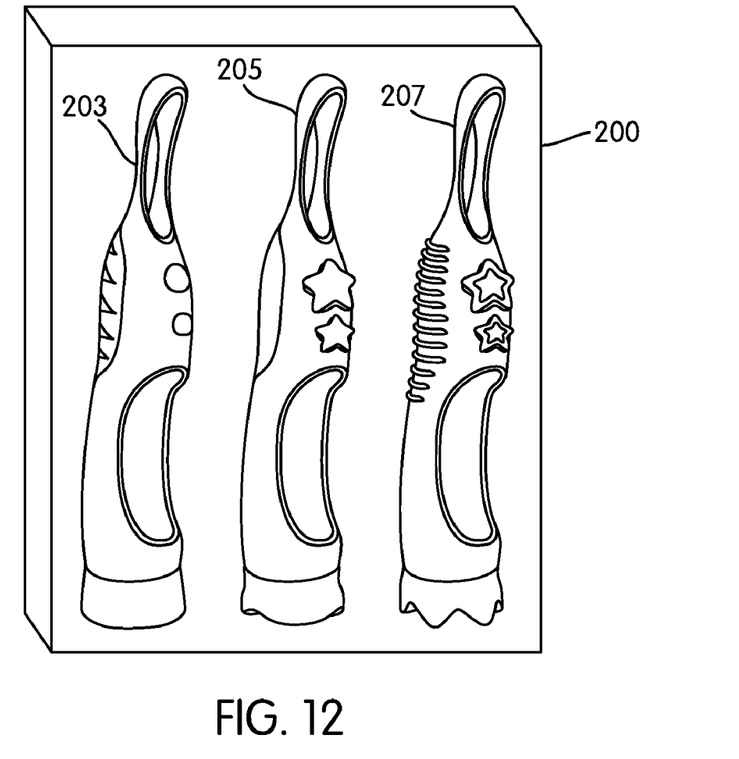

In yet another embodiment illustrated in FIG. 12, a plurality of sleeves 203-207 can be provided as a kit 200 for a toothbrush. In operation, a user may substitute a first sleeve 203 with another sleeve 205 or 207 with different visual appearances or textual compositions. For example, a kit may contain sleeves along a common theme a particular mass media show or program, but have different characters or features of the show. Thus, for example, the stylized sculptural representation of a show character could be formed by contours and/or variations in thickness of sleeve 16. Various different sleeves could be provided to enable a purchaser the ability to select his or her favorite or sleeve shapes. In these ways, a consumer is provided with a kit having a system that can be used for a variety of thematic functions. Advantageously, the consumer can selectively change the appearance of a toothbrush at a desired time period and to entice a child to be interested in brushing their teeth. In a further advantage, marketing and promotional activities can be greatly enhanced with the interchangeable constructions of sleeves and bottom portions.

Hence, a child can use the three-dimensional graphical section 17 or sleeve 16 for entertainment which is believed to provide increased use of the toothbrush for improved oral care. In one construction, the appearance of the toothbrush can have various predetermined themes or simulations of popular toys or mass media associated with children, such as television shows and computer games with action figures or other characters

What is claimed is:

1. An oral care implement comprising:
   a head and a body; and
   a sleeve extending along at least a portion of the body and the head, wherein the body includes a graphical region comprising an ornamental three dimensional sculpture and the sleeve includes at least one aperture through which the graphical region is exposed for viewing;
   wherein the ornamental three dimensional sculpture is either: (1) molded with the body to form a unitary element; or (2) an interchangeable insert for the body.

2. The oral care implement of claim 1, wherein the sleeve is resilient.

3. The oral care implement of claim 1, wherein the sleeve is removably attached to the head.

4. The oral care implement of claim 1, wherein the sleeve further comprises a resilient releasable stand.

5. The oral care implement of claim 1 wherein the body comprises a top portion that is removably connected to a bottom portion and wherein the bottom portion is interchangeable with a different bottom portion.

6. The oral care implement of claim 1, wherein the sleeve comprises an elastomeric material.

7. The oral care implement of claim 1, wherein the head includes a first mating portion and the sleeve includes a cooperative second mating portion for removably attaching the sleeve.

8. The oral care implement of claim 1, wherein the body further comprises a neck attached to the head, wherein a ratio of a length of the neck to a length of the oral care implement ranges between 20% to 30%.

9. The oral care implement of claim 1, further comprising a top end and a bottom end, wherein the body further comprises a neck attached to the head and wherein a ratio defined by a length of the neck to the top end; to a length of the oral care implement, ranges between 15% to 25%.

10. The oral care implement of claim 1, wherein the length of the oral care implement ranges between 162 cm to 194 cm.

11. The oral care implement of claim 1, wherein a width of the body ranges from 19 cm to 28 cm.

12. The oral care implement of claim 1, wherein a depth of the body ranges from 19 cm to 21 cm.

13. The oral care implement of claim 1, wherein the sleeve includes a graphical label pertaining to an entertainment program.

14. The oral care implement of claim 1 wherein the ornamental three dimensional sculpture is formed of an elastomeric material.

15. The oral care implement of claim 1 wherein the ornamental three dimensional sculpture comprises a cartoon character, a logo, a mass media figure, a sports team mascot or a totem pole.

16. The oral care implement of claim 15 wherein the ornamental three dimensional sculpture is an interchangeable insert for the body and is formed as a contoured removable plate.

17. An oral care implement, comprising:
    a head and a body having a bottom end;
    a resilient stand convertible between a first position in which an end portion of the resilient stand is directed towards the head and a second position in which the end portion of the resilient stand is directed away from the head; and
    wherein the end portion of the resilient stand is located between the bottom end of the body and the head when the resilient stand is in the first position and the bottom end of the body is located between the end portion of the resilient stand and the head when the resilient stand is in the second position.

18. The oral care implement of claim 17, wherein the resilient stand, in the second position, provides support for maintaining the oral care implement in an upright position.

19. The oral care implement of claim 17, wherein the resilient stand is replaceable.

20. An oral care implement comprising:
    a head and a body; and
    a sleeve extending along at least a portion of the body, wherein the body includes a graphical region comprising an ornamental three dimensional sculpture and the sleeve includes at least one aperture through which the graphical region is exposed for viewing;
    wherein the ornamental three dimensional sculpture is either: (1) molded with the body to form a unitary element; or (2) an interchangeable insert for the body.

21. An oral care implement, comprising:
    a head and a body having a bottom end;
    a resilient stand extending between a first end portion and a second end portion, the resilient stand convertible between a first position in which the first end portion of the resilient stand is directed towards the head and a second position in which the first end portion of the resilient stand is directed away from the head; and
    wherein the second end portion remains in a fixed position relative to the body during conversion of the resilient stand between the first position and the second position.

* * * * *